US010215668B2

(12) United States Patent
Novaro

(10) Patent No.: US 10,215,668 B2
(45) Date of Patent: Feb. 26, 2019

(54) AIR QUALITY TEST UNIT AND PROCESS

(71) Applicants: Luigi Novaro, Pembroke Pines, FL (US); Randy Miller, Pembroke Pines, FL (US)

(72) Inventor: Luigi Novaro, Pembroke Pines, FL (US)

(73) Assignees: Luigi Novaro, Pembroke Pines, FL (US); Randy Miller, Pembroke Pines, FL (US)

( * ) Notice: Subject to any disclaimer, the term of this patent is extended or adjusted under 35 U.S.C. 154(b) by 251 days.

(21) Appl. No.: 15/377,286

(22) Filed: Dec. 13, 2016

(65) Prior Publication Data

US 2017/0089810 A1    Mar. 30, 2017

Related U.S. Application Data

(63) Continuation-in-part of application No. 15/088,646, filed on Apr. 1, 2016, now Pat. No. 9,952,123.

(60) Provisional application No. 62/149,228, filed on Apr. 17, 2015.

(51) Int. Cl.
*G01N 1/00* (2006.01)
*G01N 1/22* (2006.01)
*G01N 33/00* (2006.01)
*G01N 15/06* (2006.01)
*G01N 15/00* (2006.01)

(52) U.S. Cl.
CPC ....... *G01N 1/2247* (2013.01); *G01N 15/0606* (2013.01); *G01N 33/0011* (2013.01); *G01N 2001/227* (2013.01); *G01N 2001/2223* (2013.01); *G01N 2015/0046* (2013.01)

(58) Field of Classification Search
CPC .... G01N 1/2247; G01N 1/2813; G01N 1/312; G01N 2001/005; G01N 2001/2833; G01N 2001/227; G01N 2001/2223; G01N 33/0011; G01N 15/0606; G01N 2015/0046
See application file for complete search history.

(56) References Cited

U.S. PATENT DOCUMENTS

| 5,188,963 | A  | * | 2/1993 | Stapleton | B01L 3/5023 204/462 |
| 6,103,201 | A  | * | 8/2000 | Green | A61L 9/122 239/289 |
| 6,786,105 | B1 | * | 9/2004 | Sioutas | G01N 1/2273 73/863.22 |
| 9,534,990 | B2 | * | 1/2017 | Smith | B01L 7/00 |

(Continued)

*Primary Examiner* — Blake A Tankersley
(74) *Attorney, Agent, or Firm* — Robert C. Kain, Jr.

(57) ABSTRACT

An air quality test unit for attachment to a vent of a HVAC system with air flow there through. The air quality test unit is a closeable collection container is used with only one substrate panel. The substrate panel with the collection container has one or more ball and socket pivot hinges coupling the substrate panel to the clip. The air quality test unit is attachable to the vent by the clip. The collection container of the substrate panels capture airborne substances and contaminants emanating from the air flow of the HVAC system vent and is then closed with a detachable cover. A culture growth medium may be disposed in the collection container. The air quality test unit kit provides a user with an air quality test unit and process for shipping the unit to the laboratory for analysis.

16 Claims, 16 Drawing Sheets

(56) References Cited

U.S. PATENT DOCUMENTS

2007/0092401 A1* 4/2007 Liao .................. A61B 10/0038
422/400
2013/0084624 A1* 4/2013 Waku ...................... C12Q 1/24
435/253.6

* cited by examiner

Wall Vent

Floor Vent

Ceiling Vent

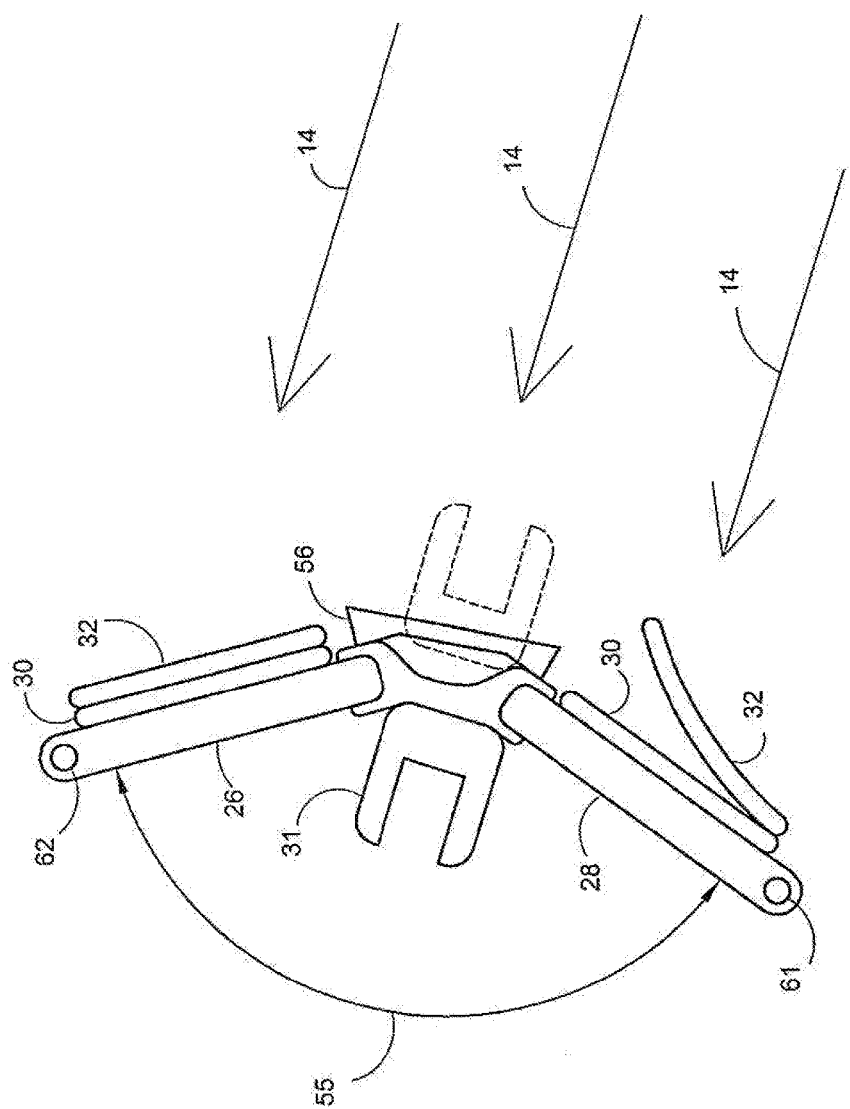

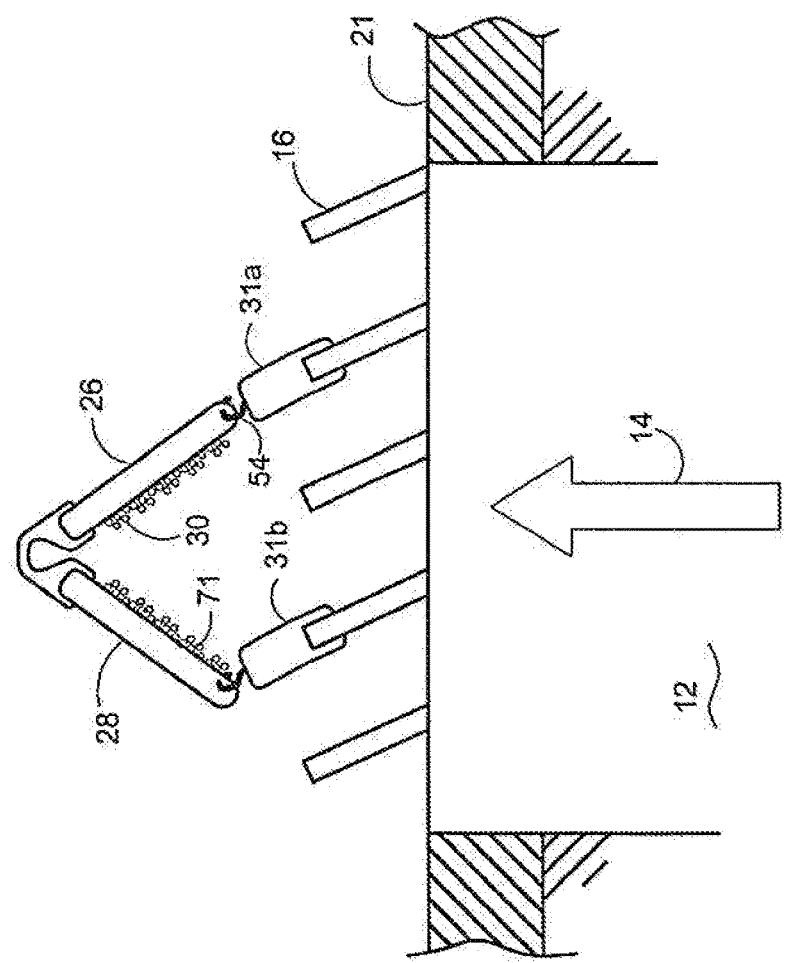

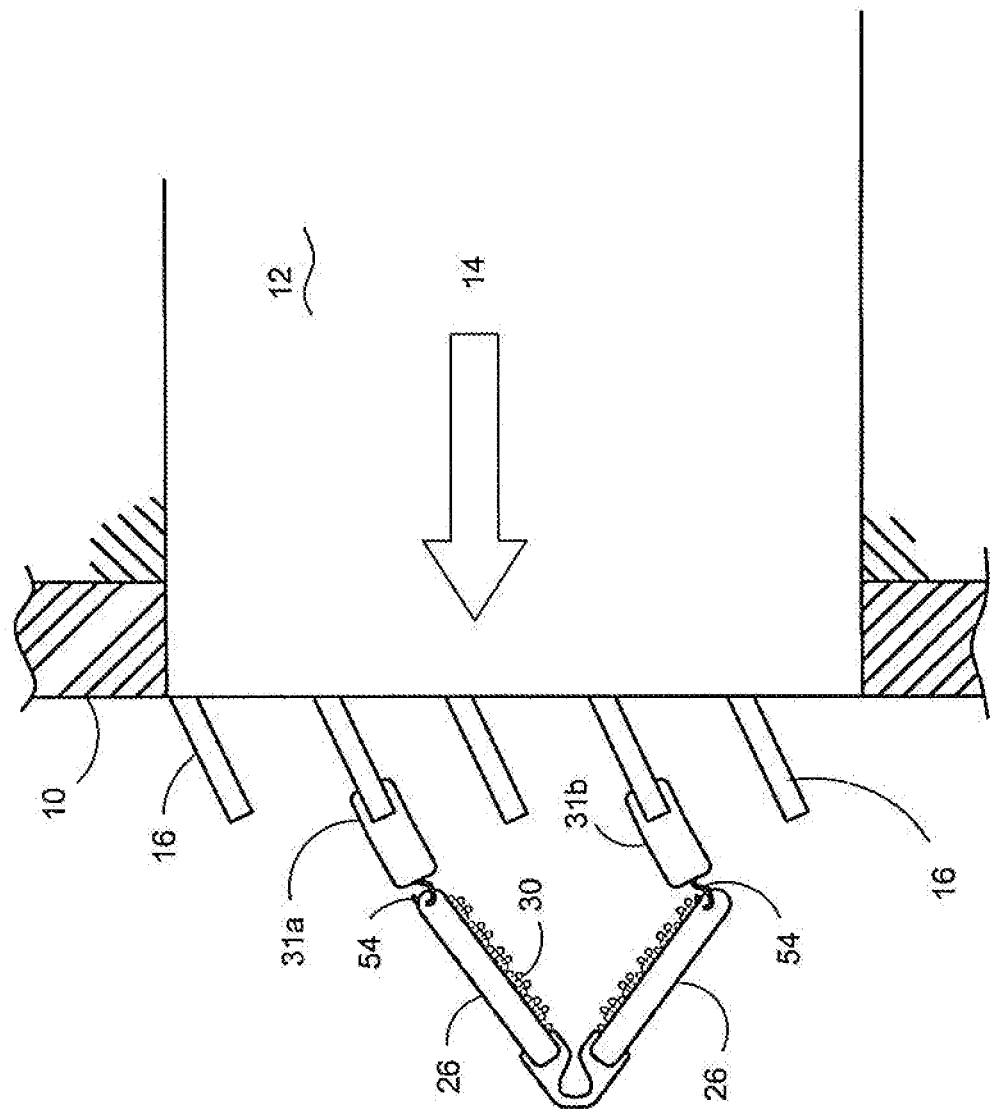

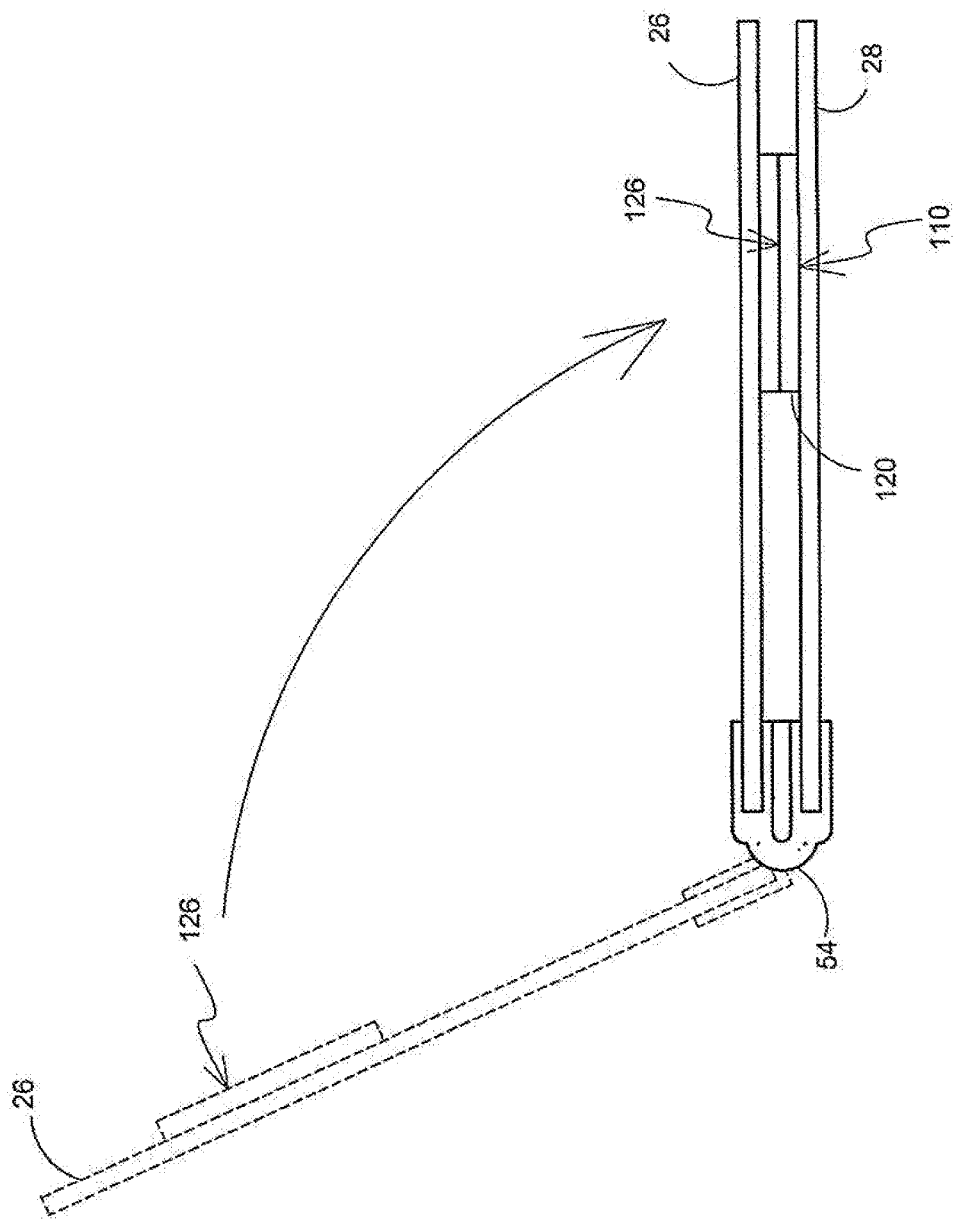

Wall vent

Floor Vent

AIR QUALITY TEST UNIT AND PROCESS

This is a Continuation-in-part under 35 U.S.C. § 120 of non-provisional patent application Ser. No. 15/088,646 filed Apr. 1, 2016 entitled Air Quality Test Unit and Process that claims the benefit of an earlier filed provisional application under 35 U.S.C. § 119(e) to Application No. 62/149,228 filed Apr. 17, 2015 the contents of which is incorporated herein by reference thereto.

The present invention relates to an air quality test unit and kit for attachment to a vent of a heat, ventilation and air conditioning systems (herein "HVAC systems," sometimes HVAC ducts only carry heated air and not AC flows). The air quality test unit is attachable to the vent blades of a vent from which air flows there through. The air quality test unit includes at least two substrate panels with at least one sticky surface or at least one collection container, and which attaches to a vent blade by one or more clips. The substrate panels take a v-shape form and the sticky surface or the collection container of the panels capture any airborne substances in the air flow from the vent. The air quality test unit may also be made of one panel with a collection container and bendable about one or more pivot joints and attachable to a vent blade by one or more clips. The air quality test unit is then sent to a laboratory for testing to reveal the air quality and airborne substances or pollutants found therein. The process operates to gather airborne particulate on the sticky surface or in the collection container while the panels are mounted on the HVAC vents, closing the panels or putting the cover on the container, delivering the same to a laboratory for analysis and reporting the results to the consumer.

BACKGROUND OF THE INVENTION

Air quality has become an increasing concern. The air inside homes, offices, and other buildings can be more polluted than the air outside. The Environmental Protection Agency estimates that indoor air can be two to five times more polluted than the air outdoors. The air inside your home may be polluted by lead, formaldehyde, fire-retardants, radon, smoke, even volatile chemicals from fragrances used in conventional cleaners. Further there are allergens in homes and buildings that includes microscopic dust mites, mold and pet dander. Children, people with asthma, and the elderly may be especially sensitive to indoor pollutants.

Indoor allergens and irritants have become much more important in recent years, because people are spending more time indoors. Also, there has been an increase in the number and severity of allergies. Therefore there is an increased need to have duct work cleaned in HVAC systems and cleaner HVAC systems in general. There is also a need for quick and reliable methods and devices for testing and qualifying the quality of air within the home.

One previously known air testing device used a flat sampler patch attachable with pins to the air filter of the HVAC duct system. This tested the air entering the HVAC unit, but not specifically the air exiting the HVAC unit. Other test kits involved testing for mold and fungal elements or spores by swabbing a surface to be tested. This test only captured mold and fungal elements or spores that had settled out of the air and onto a surface and not airborne substances. Other test systems required the use of a fan to draw particles onto a collection surface.

The Jossam company discloses a flat sampler patch attached by pins onto an air filter (the filter being disposed in the HVAC system air intake). Josamm also discusses a fan method of testing, which is a flat patch sampler attached to a fan to test indoor home or business environments. <www-.jossam.biz>. The Health Goods company describes a health check system designed to collect mold and fungal elements/spores that settles out of the air onto a surface. The user swabs the surface to be tested, performs the test and sends the test sample in a postage prepaid envelope to an accredited laboratory for analysis. <www.healthgoods.com>. Prisim Analytical Technologies, Inc., discloses a home air check system that has a small pump and associated items to capture particulate in the air flow. <www.homeaircheck-.com>. The Prisim kit identifies over 400 volatile organic compounds, formaldehyde, growing mold, secondhand smoke and more, and offers an easy-to-use test kit, wherein after particulate collection, the kit is sent to an accredited laboratory.

U.S. Pat. No. 2,079,474 shows a hand pump with a slide. When the user pulls air into the cylinder, the particulate in the air is captured by the slide at the end of the plunger in the cylinder. The system tests for dust or microbic content of air. The collector is a pump consists of a cylinder open at one end. At its other end is a removable cap. A plunger is movable in the cylinder. Slots in a slide are disposed crosswise in a tube. The slots have a suitable adhesive substance to hold the dust or microbic particles. The slide is then removed and the slide is examined.

U.S. Pat. No. 6,103,201 discloses an air freshener with a clip for a HVAC vent. U.S. Pat. No. 6,030,427 discloses a replaceable air filter apparatus for filtering the air in the home. The HVAC filter casing has a hinge on a register that controls the flow of air through the duct work. Korean Patent No. KR 20080092192 discloses a collector base plate for collecting microorganisms in air. The base plate has an adhesive coating. A motor drives air through nozzle and onto the collector base plate. The adhesive compositions coated on one side of the base plates capture particles in the discharged air.

Swiss Patent No. CH 684610 discloses a multistage aerosol particle collector encapsulated in a metal tube. The tube end has a suction cap and an orifice and a suction nozzle. The nozzle sucks in air and the air has suspended particles. U.S. Pat. No. 8,668,758 discloses a nonwoven filtration media comprising a tackifier is added to the nonwoven filtration media to provide a sticky or adhesive surface on the fibers, has an advantageous combination of stiffness, foldability, efficiency and the ability to retain a fold.

Objectives of the Invention

It is an objective of the present invention to provide an air quality test unit and kit that is attachable to the vent blades of a HVAC vent. There is a need for an air quality test unit that is easy to use by a home owner and that simply attaches to a vent for a predetermined amount of time.

It is an object of the present invention to provide an air quality test unit that is positioned on the vent such that it captures a representative sample of the airborne substances or pollutants emanating from the HVAC system. There is also a need for an air quality test unit that can rapidly and accurately be tested for a variety of common airborne pollutants and contaminants.

It is a further object of the present invention to provide an easy to use and highly accurate air quality test unit and kit. There is a need for air quality test unit and kit that is highly accurate, reliable and easy to use. There is also a need for an air quality test unit that adequately protects the airborne contaminant sample after the sample is obtained and while it is being packaged and shipped to the laboratory for testing.

SUMMARY OF THE INVENTION

The present invention provides an air quality test unit designed to capture and retain the airborne substances and contaminants emanating from a HVAC system for analysis. The air quality test unit attaches to a vent of a heat, ventilation, air conditioning (HVAC) system with air flow there through. In one embodiment, the air quality test unit includes two substrate panels each having respective sides. At least one of the substrate panels has a side covered with a sticky substance, thereby forming a sticky surface, that is initially covered by a removable layer. This removable layer is removed by the consumer or user when the test unit is operational. At least one clip (preferably two clips) is secured to at least one substrate panel or a hinge. The clip attaches the unit to the HVAC vent vane wherein the substrates have a v-shaped form. The substrate panels are hinged together and partially rotate with respect to each other. If the panels are normal (perpendicular) to the vent air flow, this disrupts the flow. Although such normal (perpendicular) positioning works, the more efficient angular position is at an obtuse angle with respect to the air flow such that air passes over the sticky side of the panel which results in maximizing the potential to collect airborne particulate.

After removal of the removable layer and when the substrate panels are held on the vent in a v-shaped position on the vent vane, the sticky surface captures airborne substances in air flow passing over the sticky surface (the air flow emanating from the HVAC system vent). The substrate panels are held in an open v-shaped position or form by the hinge and the clip combination. When the air quality test is complete (after a predetermined period of time), the user removes the v-shaped test kit from the vent vanes, closes the panels via the hinge thereby allowing one substrate panel to be rotated towards the other panel and away from the stop such that one panel faces the sticky surface of the other panel. In a preferred embodiment, both panels have sticky surfaces which, when loaded with particulate, close and collapse towards each other, however the sticky surfaces of the panel do not contact each other. This closure can be used to prevent the particulate on the interfacing and adjacent surfaces of the closed panel system from being removed. This panel closure allows the air quality test unit to be packaged and shipped while retaining all airborne substances or contaminants on the sticky surface(s) for analysis.

An air quality test unit for attachment to a vent of a heat, ventilation, air conditioning (HVAC) system with air flowing there through comprises at least two substrate panels each having respective sides, at least one substrate panel having a corresponding side with a sticky surface that is covered by a removable layer. A hinge couples the substrate panels about which the substrate panels rotate. There is at least one clip secured either to at least one substrate panels or the hinge, the clip adapted to attach to the vent. The substrate panels have a first operative mode in a V-shape configuration and a second operative mode in a closed configuration. After removal of the removable layer, the substrate panels are position in the V-shaped mode with the clip adapted to be attached to said vent such that the sticky surface captures airborne substances in air flow from the vent and in the second closed mode the sticky surface is protectively coverer by one or the other substrate panel.

The present invention also provides a process for measuring an air quality of air flow emanating from a heat, ventilation, air conditioning (HVAC) system with a laboratory analysis. The air quality test unit is attached to a vent of a HVAC system, when there is air flow through the HVAC system. The air quality test unit collects airborne substances from the vent air flow. The air quality test unit includes at least two substrate panels with at least one panel having a sticky surface that is temporarily covered by a removable layer. At least one clip secures the substrate panels to the vent. A hinge allows the panels to rotate towards and away from each other and allows the substrate panels to take a v-shape form at an acute panel-to-panel angle which sets up a v-shaped air flow interrupter surfaces channeling air flow over sticky panel surfaces from the vent air flow when attached to a ceiling vent. When used on a floor vent or a wall vent, the sticky panels face each other on the inside of the v-shape form such that the air flows directly into the sticky surfaces of the substrate panel.

A removable layer is removed from the sticky surface of the substrate panel. The air quality test unit is left on the vent for a predetermined time. After the predetermined time, the air quality test unit is removed from the vent. The substrate panels are closed and collapsed toward each other by rotating one panel onto the other panel, wherein the sticky surfaces face each other. In the closed position, the sticky surfaces of the substrate panels face each other, but do not touch. The collapsed air quality test unit (with panel-to-panel adjacent surfaces) is delivered to a laboratory for analysis. The lab tests for particulate on the panels. The laboratory analysis results are then reported setting forth air quality for the air flow.

In another embodiment of the air quality test unit, a closeable collection container is used with only one substrate panel. The substrate panel with the collection container has one or more ball and socket pivot hinges coupling the substrate panel to the clip. A collection pad is disposed on the collection container base. There is a detachable collection container cover and at least one pivot hinge coupling the substrate panel to a clip. The clip is secured to at least one pivot hinge and adapted to attach to the vent. The collection cover is removed and the substrate panel is positioned to be in the air flow with the clip attached to the vent such that the collection container captures airborne substances in air flow from the vent. The collection pad in one embodiment is a thin fibrous material which captures, holds and maintains the yeast or mold until testing. The collection pad can be a thin fibrous material that contains dehydrated growth or culture media. After the airborne substances are captured in the collection container, the collection container is closed by the collection container cover and sent out for analysis.

BRIEF DESCRIPTION OF THE DRAWINGS

The subject matter which is regarded as the invention is particularly pointed out and distinctly claimed in the claims at the conclusion of the specification. The foregoing and other objects, features, and advantages of the invention will be apparent from the following detailed description when taken in conjunction with the accompanying drawings.

FIG. 1A is a side view of a HVAC wall duct and vent with an air quality test unit attached to a vent blade.

FIG. 1B is a side view of a HVAC floor duct and vent with an air quality test unit attached to the vent blades.

FIG. 2 is close up side view of a HVAC ceiling duct and vent with an air quality test unit.

FIG. 3 is a side view of an air quality unit.

FIG. 4a is a side view of a HVAC floor duct and vent with an air quality unit.

FIG. 4b is a side view of a HVAC wall duct and vent with an air quality unit.

FIG. 11 is a side view of the embodiment of FIG. 10 for the air quality test unit with a collection container.

FIG. 12 A is a side view of a HVAC wall duct and vent with an air quality test unit with one substrate panel and a collection container attached to a vent blade.

FIG. 12 B is a side view of a HVAC floor duct and vent with an air quality test unit with one substrate panel and a collection container attached to the vent blades.

Figure 13:
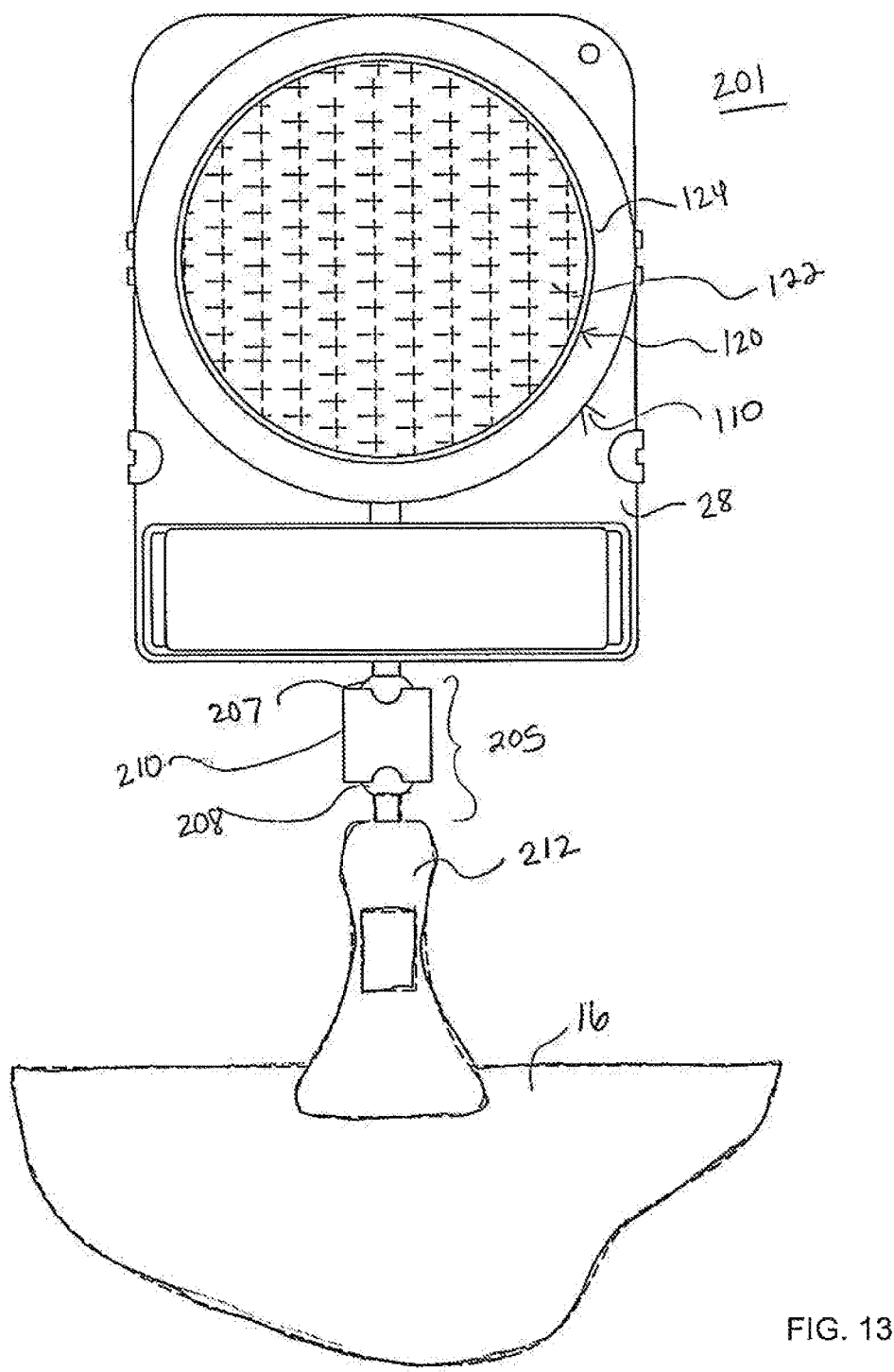

FIG. 13 is a front elevational view of an air quality test unit with an axially aligned universal joint.

Figure 14:
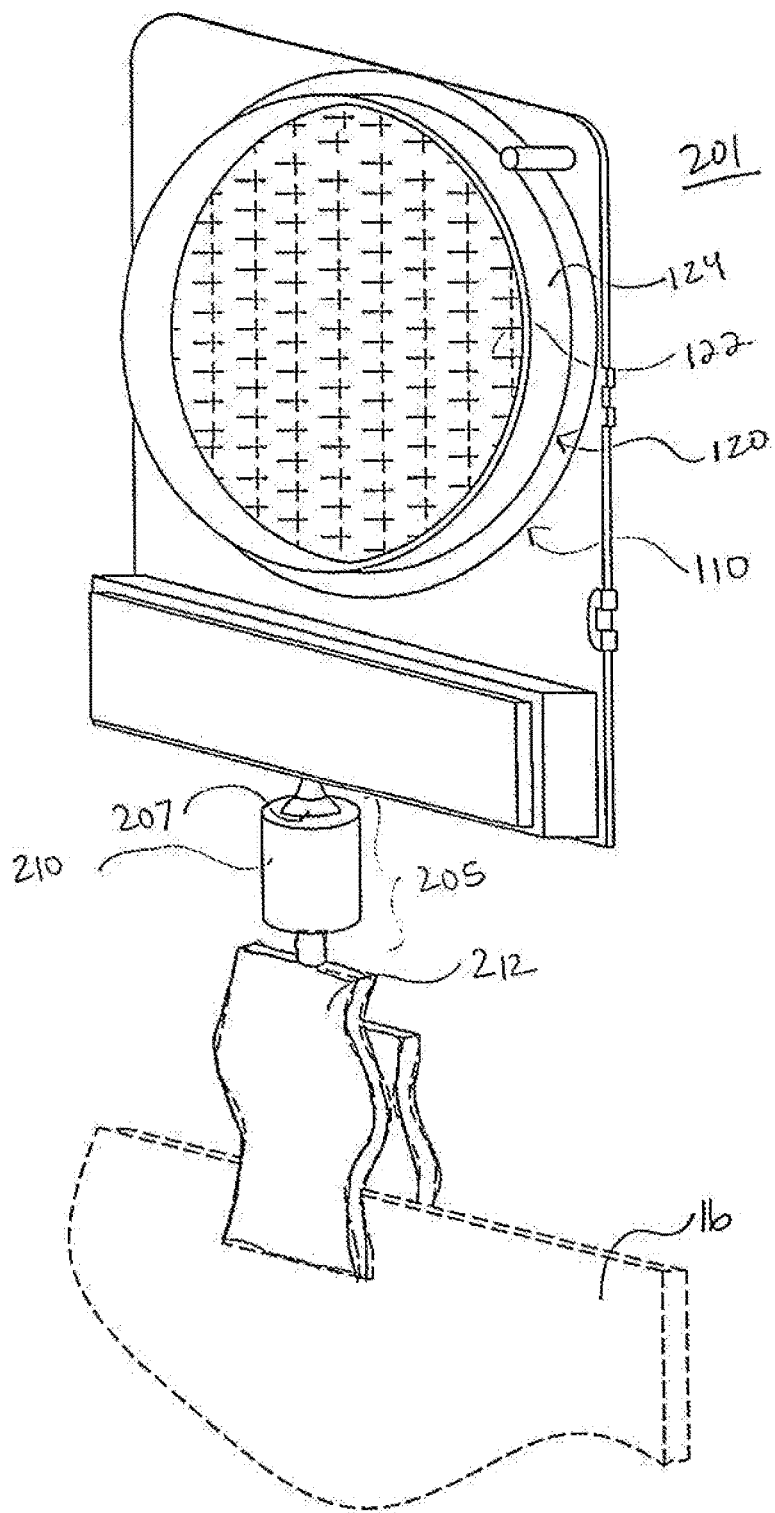

FIG. 14 is a perspective view of the air quality test unit with the axially aligned universal joint.

Figure 15:
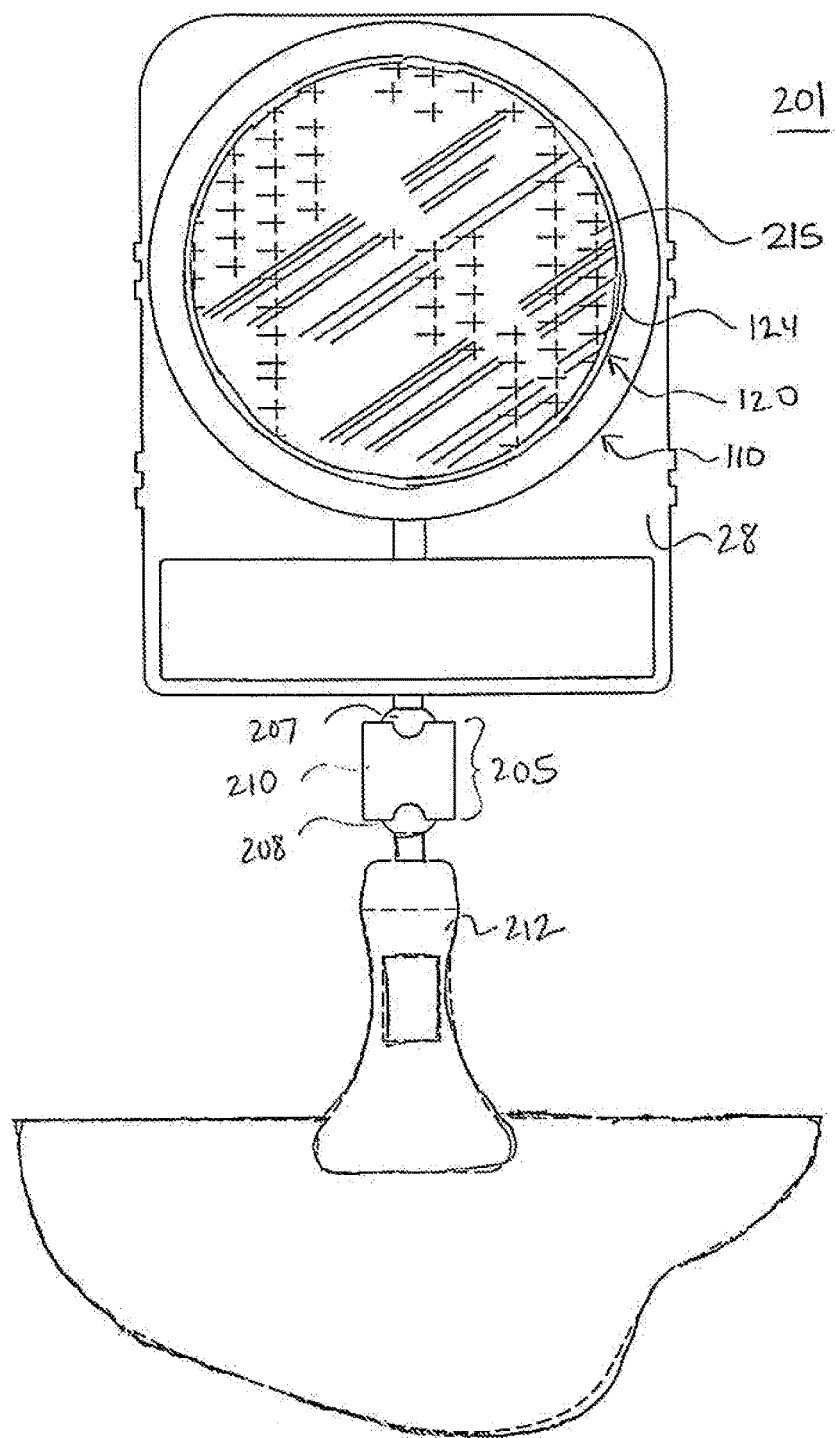

FIG. 15 is an air quality test unit with a universal joint and a collection pad covered by a collection container cover.

DETAILED DESCRIPTION OF THE PREFERRED EMBODIMENTS

Referring now to the drawings, the invention will be described in more detail. Further objects and advantages of the present invention are illustrated in the drawings and are discussed hereinafter. Similar numerals designate similar items in the diagrammatic drawings FIGS. 1-16. It is important to note that the embodiments of the invention described below are only examples of the several advantageous uses of the innovative teachings described herein. In general, statements made in the specification of the present application do not necessarily limit any of the various claimed inventions. Moreover, some statements may apply to some inventive features but not to others. In general, unless otherwise indicated, singular elements may be in the plural and vice versa with no loss of generality.

Figure 1A:
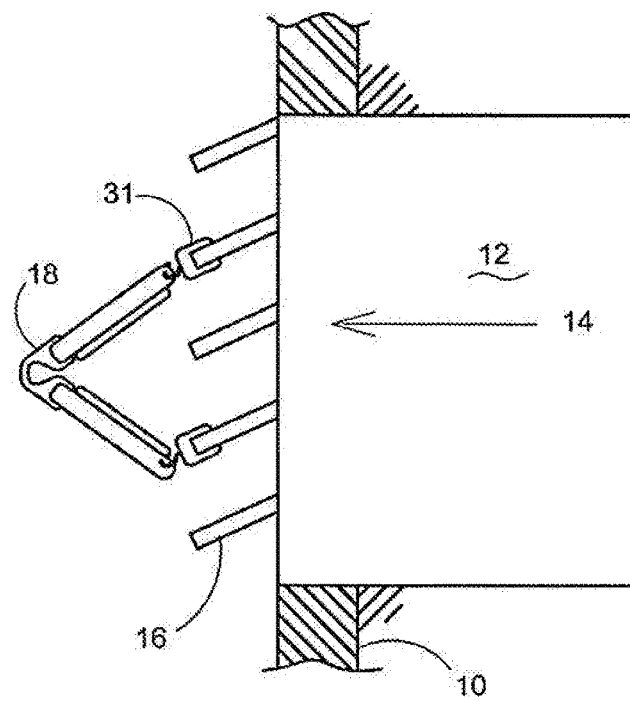
Figure 1B:
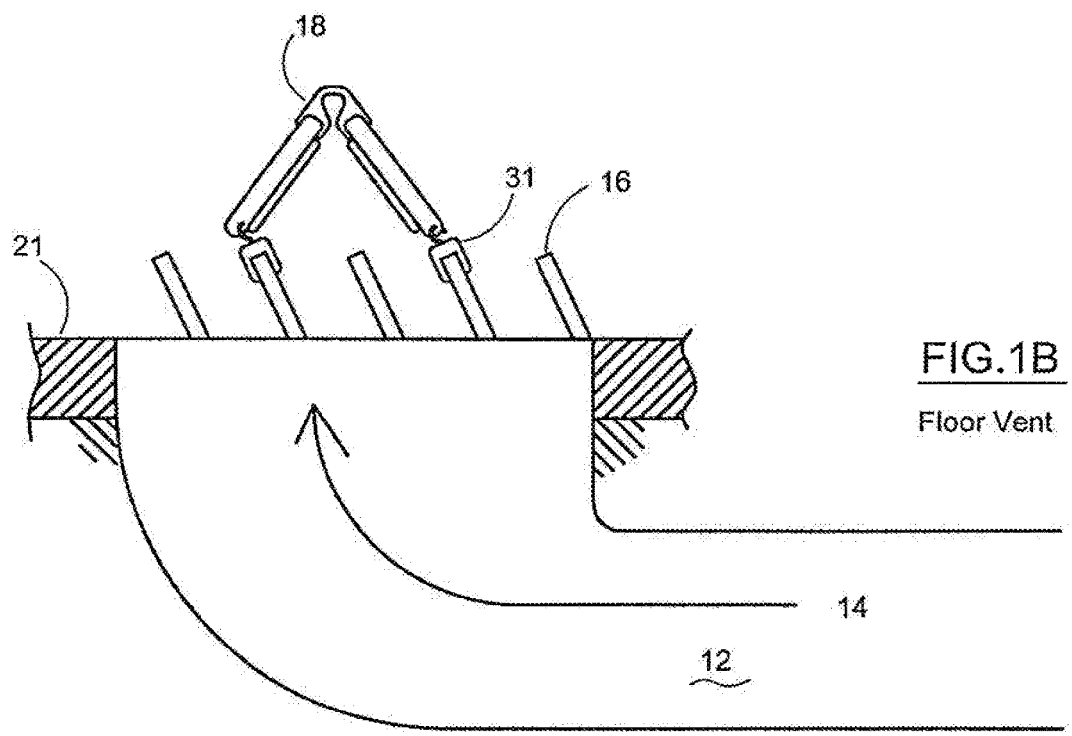

FIG. 1A is a side view of a HVAC wall duct and vent with an air quality test unit attached to the vent blades or vent vanes. The vent blades channel air from the HVAC duct work into the interior space of the building. FIG. 1A shows the HVAC duct 12 carrying air flow 14 towards and out of the vent 16. In FIG. 1A, the vent is in the wall 10. In some building construction, typically in warmer, southern climates, the HVAC ducts are located in the ceilings and walls such that vents can be placed either in the ceilings or the walls of the building. The air quality test unit 18 is removably attached to the blades of the vent 16. FIG. 1B shows a similar air quality test unit 18 attached to the vent blades wherein vent 16 is disposed in the floor 21. In building construction in colder, northern climates, HVAC duct work is placed under the flooring. In the wall and floor vent 16 mounts, the air quality test unit 18 has two clips 33 that attach to two vent blades.

Figure 2:
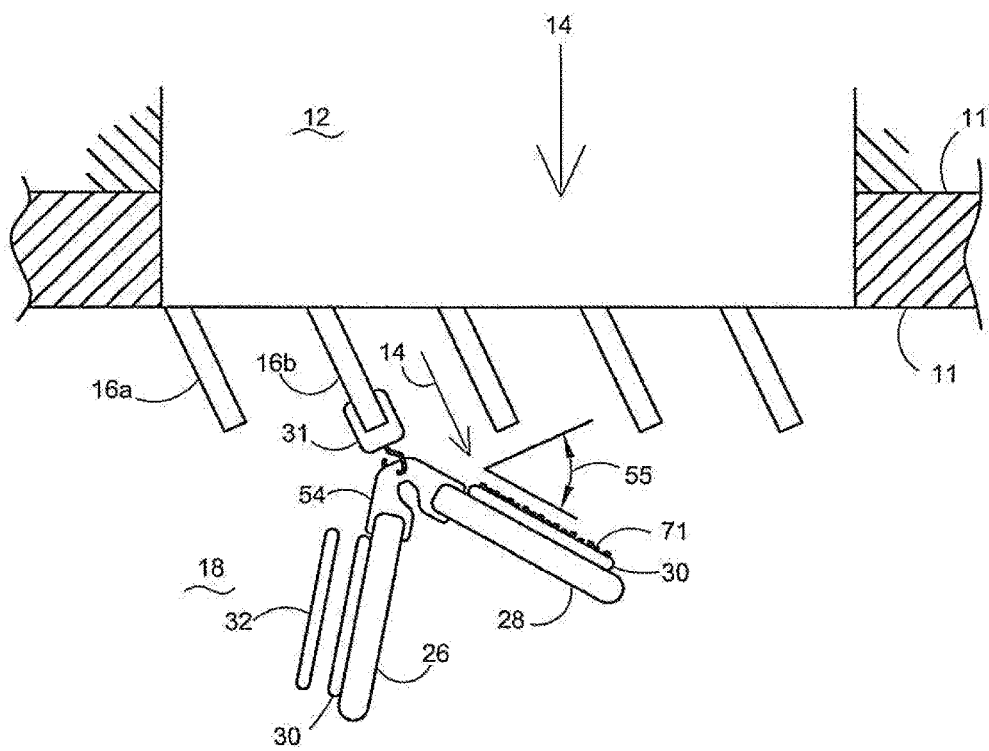
Figure 7:
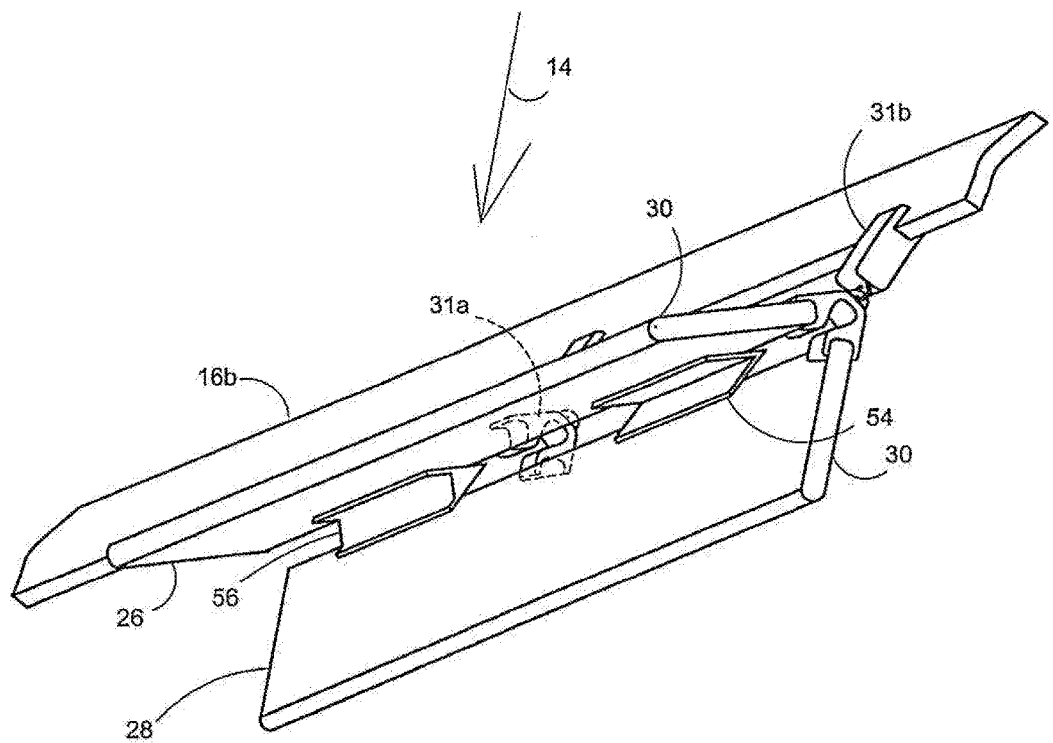
FIG. 7 is a diagrammatic view of the air quality test unit attached to a blade or vane of a ceiling vent.
Figure 8:
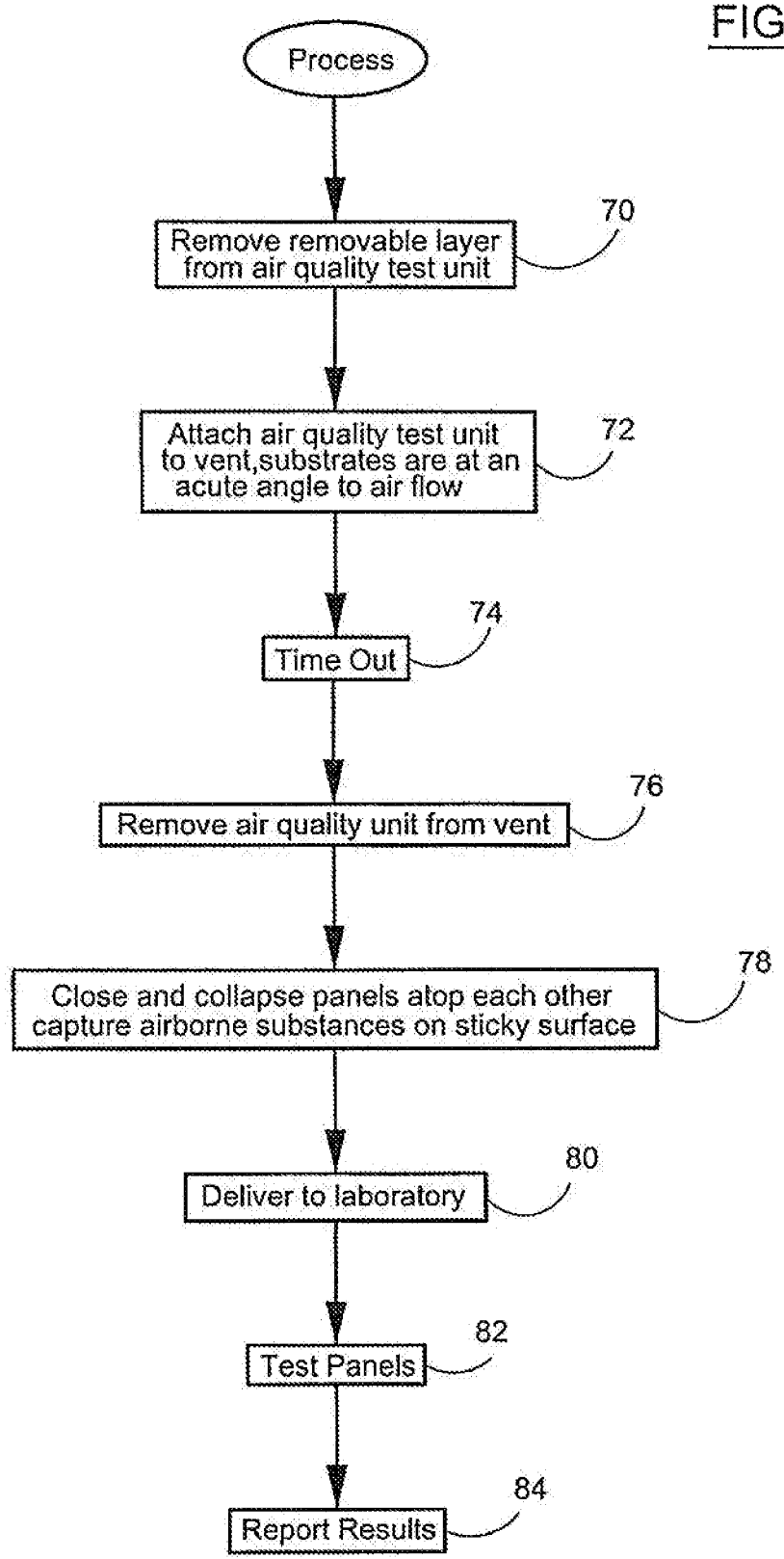
FIG. 8 is a flow chart of the process of use of the air quality test unit.

FIG. 2 shows the details of the air quality test unit 18 attached to a vent in the ceiling 11. The air quality test unit 18 is shown in the first operative mode in a V-shape configuration. Vent blade or vane 16a is upstream of the air quality test unit 18. Air quality test unit 18 is attached to blade 16b by one or more clips 31 secured to the hinge 54. The clip 31 includes any known structure that serves to attach items together, such as a clip on a ring, a clip attached to a "C" clip, a clip rotatably attached to a "C" clip, a pressure actuated clip, etc. A second clip can be attached on the other outer edge of the air quality test unit hinge, where the substrate panels 26, 28 meet (as shown in FIG. 7). Thus there can be two clips 31 attached on the outer edges of the hinge 54, which is the interface where the substrate panels 26, 28 are connected. The air quality test unit 18 has two substrate panels 26, 28 that rotate with respect to each other, right substrate panel (herein "R-substrate panel") 26 and left substrate panel (herein "L-substrate panel") 28. Each substrate panel 26, 28, has a removable layer 32, that is removed prior to the testing. This layer covers the panel's sticky surface 30. The removable layer 32 may be any known material, such as paper or plastic, which serve to protect and seal the sticky surface 30 prior to use. When removable layer 32 is withdrawn or peeled from the substrate panels 26, 28, a sticky surface 30 is exposed. When the air quality test unit 18 is clipped onto vent blade 16b, via clip system 31, the sticky surfaces 30 of substrate panels 26, 28 are at an acute angle 55 to air flow 14.

The sticky surface 30 may be any known adhesive surface that is capable of collecting and preserving particles out of the air for testing. In the preferred embodiment, the sticky surface 30 is composed of a PETRIFILM, specifically designed for yeast and mold. Such a film containing petri-type agar nutrients is commercially available from 3M as PETRIFILM, a trademark of 3M. The PETRIFILM contains the nutrients found in agar and will preserve the desired live particulate (e.g. mold, bacteria, yeast) that attaches to the sticky surface 30 from the air until testing is complete. The PETRIFILM will also aid the laboratory in performing the test, as it will not have to innoculate one or more petri dishes. The testing can be performed right on the film, which is pre-calibrated. Any such film containing petri-type agar may be used as the sticky surface 30 on the unit 18.

The required or pre-set acute angle 55 is one of the several important aspects of the present invention because the acute angle 55 assures that the air flow 14 over the sticky surfaces 30 of substrate panels 26, 28 is optimal and will collect an accurate representative sample of airborne substances 71. The terms airborne substances, contaminants and pollutants shall be interchangeable herein and include airborne dust, pollen, dust mites, pet dander, mold spores, bacteria, etc.

When the air quality test unit 18 is used on a wall vent or a floor vent as shown in FIGS. 1A and 1B (and FIGS. 4A and 4B in greater detail), the substrate panels 26, 28 take a v-shape form with the sticky surface 30 on the inner side of the substrate panels 26, 28. In this embodiment, the clips 31 are secured on the distal end of the substrate panels 26, 28 and attach the unit 18 to the vent blades 16. This causes the sticky surfaces 30 to be directly in the airflow 14 from the vent. When the air quality test unit 18 is used on a ceiling 11 vent as shown in FIG. 2, the substrate panels 26, 28 take a v-shape form with the sticky surfaces 30 on the outer facing sides of the substrate panels 26, 28. In this embodiment, the clips 31 are secured on the hinge 54 and attach the unit 18 to the vent blades 16. This causes the sticky surfaces 30 to be directly in the airflow 14 from the ceiling 11 vent.

FIG. 3 shows the air quality test unit in detail. The features include a sticky layer 30 and removable layer 32. The removable layer 32 covers and protects the sticky layer 30 until the device 18 is ready to be used. When the air quality test unit 18 is ready to be used, the removable layer 32 is peeled off of the sticky layer 30 and the removable layer 32 is discarded. The clip 31 can be rotated for attachment to the vent blade. The clip 31 can be any known technology that encompasses attachment means where the clipping means secures the air quality test unit to a vent blade through grasping the blade between two opposing elements. A stop 56, or hinge stop, serves to ensure that when the substrate panels 26, 28 are opened, the angle is maintained at the optimal acute angle 55 to air flow 14 and the substrate panels 26, 28 are held in a v-shape form. The hinge 54 permits the substrate panels 26, 28 to rotate about the hinge. The stop 56 prohibits clockwise movement of L-substrate panel 28 as shown in FIG. 3. This maintains the optimal angle 55 of the panels 26, 28 to the air flow 14.

Figure 5:
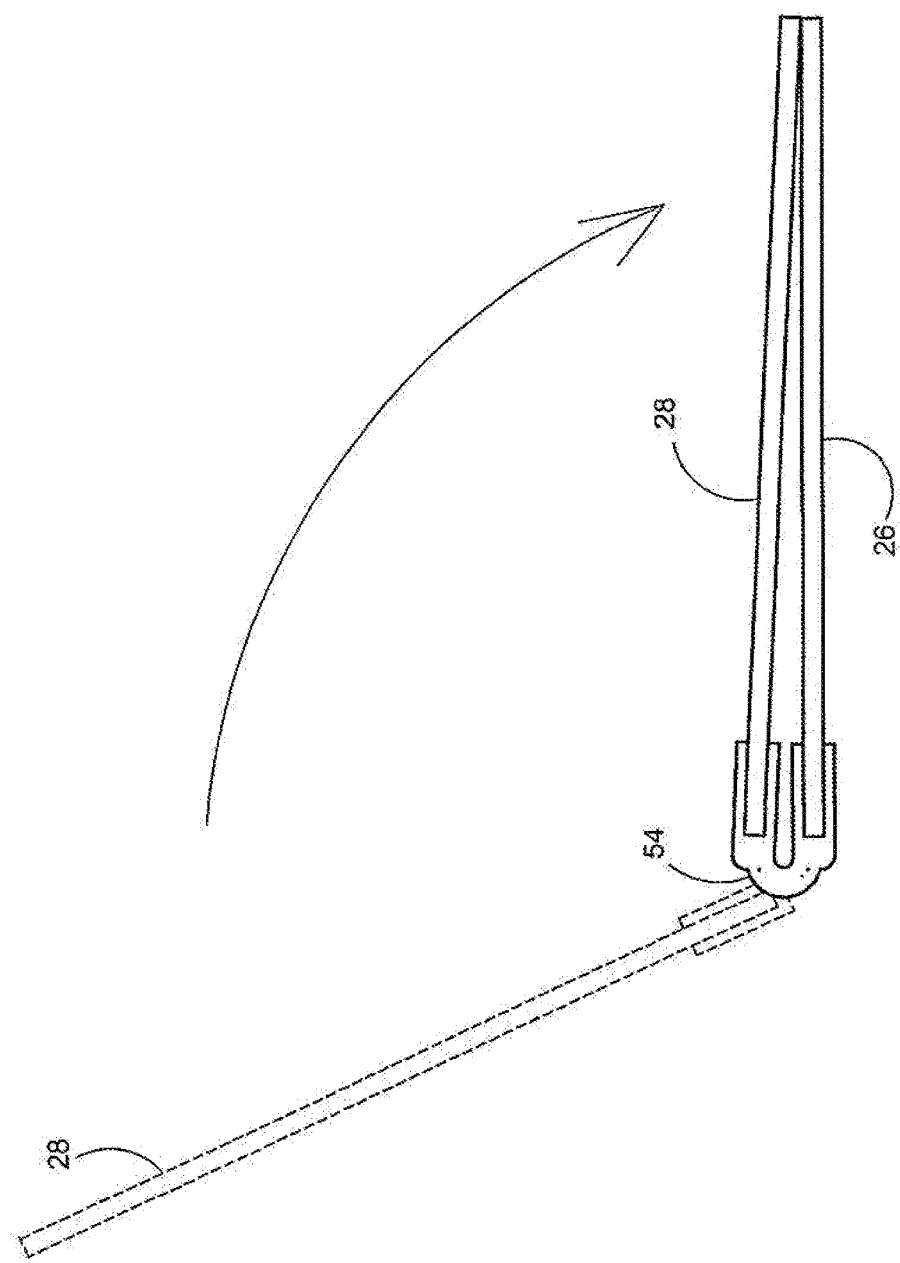
FIG. 5 is a side view of the air quality unit in a closed position.
Figure 6:
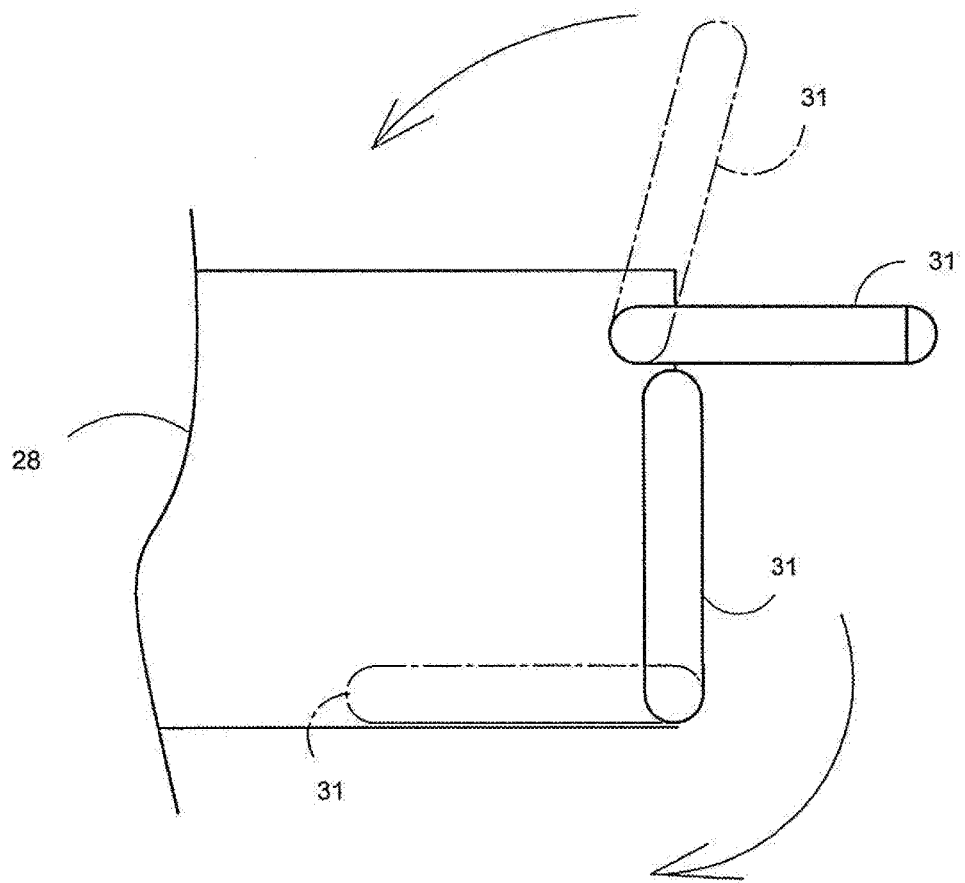
FIG. 6 is a side elevation view of an air quality test unit with hooks.

The substrate panels can swing toward each other counterclockwise, as in FIG. 5. The substrate panels 26, 28 are brought together atop one another as shown in FIG. 5, when the air quality test unit 18 has been attached to the vent for a set period of time and is ready to be sent out for testing. As shown in FIG. 3, the angle 55 provides optimal exposure to air flow 14 on substrate panels 26, 28 and sticky layers 30. Holes 61, 62 are on the distal end of the substrate panels 28, 26. Holes 61, 62 serve as attachment means for clips 52 when the vent is a floor vent and the air quality test unit needs additional support.

FIG. **4*a* is a side view of a HVAC floor duct and vent with an air quality test unit. The vent is on the floor 21. It shows L-substrate panel 28 and R-substrate panel 26 opened to the desired v-shape form. The sticky surface 30 of R-substrate panel 26 captures airborne substances 71 and retains them on the sticky surface 30. The air quality test unit 18 is attached to vent blades 16 by clips 31*a*, 31*b*. At least two clips 31*a*, 31*b* are desired to ensure the air quality unit 18 is properly supported and the desired angle 55 is maintained to the air flow 14. One or more clips 31*a*, 31*b* are attached to the distal end of each substrate panels 26, 28. One such attachment means is a clip 31 with a hook 54 that is inserted through a hole in the substrate panels 26, 28. The clips 31*a*, 31*b* may each be attached to the distal end of either substrate panel 28 and 26 and connect the air unit to the vent blades 16. The air flow 14 flows through the HVAC duct 12 and past the vent blades 16. If the air flow 14 is carrying any impurities or airborne substances 71, they will be captured and retained on the sticky surface 30 of the substrate panels 26, 28**.

FIG. **4*b* is a side view of a HVAC wall duct and vent with an air quality test unit. The vent is in the wall 10. Shown is substrate panels 26, 28 opened to the desired v-shape form with the sticky surface 30 on the inside of the v-shape form, facing into the air flow 14. The air quality test unit 18 is attached to vent blades 16 by clips 31*a*, 31*b*. The clips 31*a*, 31*b* are attached to the distal end of each substrate panels 26, 28**.

FIG. 5 shows the substrate panels 26, 28 in a closed or collapsed position after removal from the vent blades. This configuration of the air quality test unit 18 is the second closed mode configuration. In the closed position or mode, particulate is securely enclosed between the collapsed, closed panels. In this embodiment, the L-substrate panel 28 has been swung clockwise towards R-substrate panel 26 until the distal portions of the panels 26, 28 touch. The substrate panels 26, 28 are generally spaced apart with only the distal portions of the panels 26, 28 touching. This encloses and protects the airborne substances 71 that have been captured on each substrate panel's 26, 28 sticky surface 30 between the inter space of the substrate panels 26, 28. Because the sticky surfaces 30 face each other, the enclosure of the substrates upon each other ensures that no captured airborne substances 71 will be removed from the sticky surfaces 30 by physical abrasion or otherwise during packaging and transport prior to testing.

Thereafter, the closed panel system is shipped to a laboratory which tests the type of airborne substances 71 captured on the substrate panels 26, 28. These test labs can determine the type of airborne substances 71 and the amount or concentration of certain airborne substances 71 in the indoor air flow from the HVAC system. In this manner, the owner/occupant may chose the clean the vents or use better filters to capture more airborne substances 71 moving through the indoor space.

FIG. 6 shows a side elevation view of an air quality test unit 18 with two clips 31. One surface of one substrate panel 28 is shown. Attached to the substrate panel 28 are two clips 31. The clips 31 are attached to the outer corner edges of the substrate panel 28. The clips are located at the point where the two substrate panels 28 and 26 meet and interface at the hinge. In FIG. 6, substrate panel 26 is not shown, because it lies below substrate panel 28 and the panels 26, 28 contain clips 31 at the point of their interface. FIG. 6 shows that the clips 31 can rotate on the panel 28. The rotation of the clip allows the panels 26, 28 to rotate about the hinge and open and close. In this configuration, with the clips 31 on the hinge of the panels 26, 28, the air quality test unit would be attachable to a ceiling vent, as shown in FIG. 2.

FIG. 7 is a diagrammatic view of the air quality test unit attached to a vane or blade of a vent. The substrate panels 26, 28 are shown in a v-shape form as attached to the blade **16*b* of the vent by clips 31. Two clips 31 are located on the outer corner edges of the interface of the substrate panels 26, 28. Hinge 54 is located at the interface of the substrate panels 26, 28. A stop 56 holds the substrate panels 26, 28 at an acute angle to the air flow 14 and prevents inner facing sides of the substrate panels 26, 28 from contacting each other when the panels are mounted on the vent blade 16*b*. In the configuration shown in FIG. 7, the air quality test unit would be attached to a ceiling vent with the sticky surface 30 on the outer facing side of substrate panels 26, 28**.

FIG. 8 is a flow chart of the process of use of the air quality test unit. The process measures air quality of air flow emanating from a heat, ventilation, air conditioning (HVAC) system with a laboratory analysis. First, a removable layer is removed from the sticky surface of the substrate panel. See Step 70. The removable layer can be removed prior to attachment to a vent or just after attachment to a vent. The air quality test unit is attached to a vent of a HVAC system, when there is air flow through the HVAC system and the substrate panels are placed in the air flow effectuated by the substrate panels being in a v-shape form. See Step 72. The air quality test unit comprises at least two substrate panels with at least one panel having a sticky surface that is temporarily covered by a removable layer. At least one clip secures the substrate panels to the vent. A hinge allows the panels to rotate and a stop holds the substrate panels in a v-shape form directly in the air flow through the vent.

Next, the air quality test unit is left on the vent for a predetermined time. See Step 74. The predetermined time period can be as short of a duration as 1-2 hours or as long as 24 hours. After the predetermined time, the air quality test unit is removed from the vent. See Step 76. The substrate panels are closed and collapsed against each other by rotating one panel toward the other panel, wherein the sticky sides face each other. See Step 78. The collapsed air quality test unit is delivered to the laboratory for analysis. See Step 80. The laboratory analyzes and tests the panels. See Step 82. The laboratory analysis results are reported setting forth air quality for the air flow. See Step 84.

Figure 9:
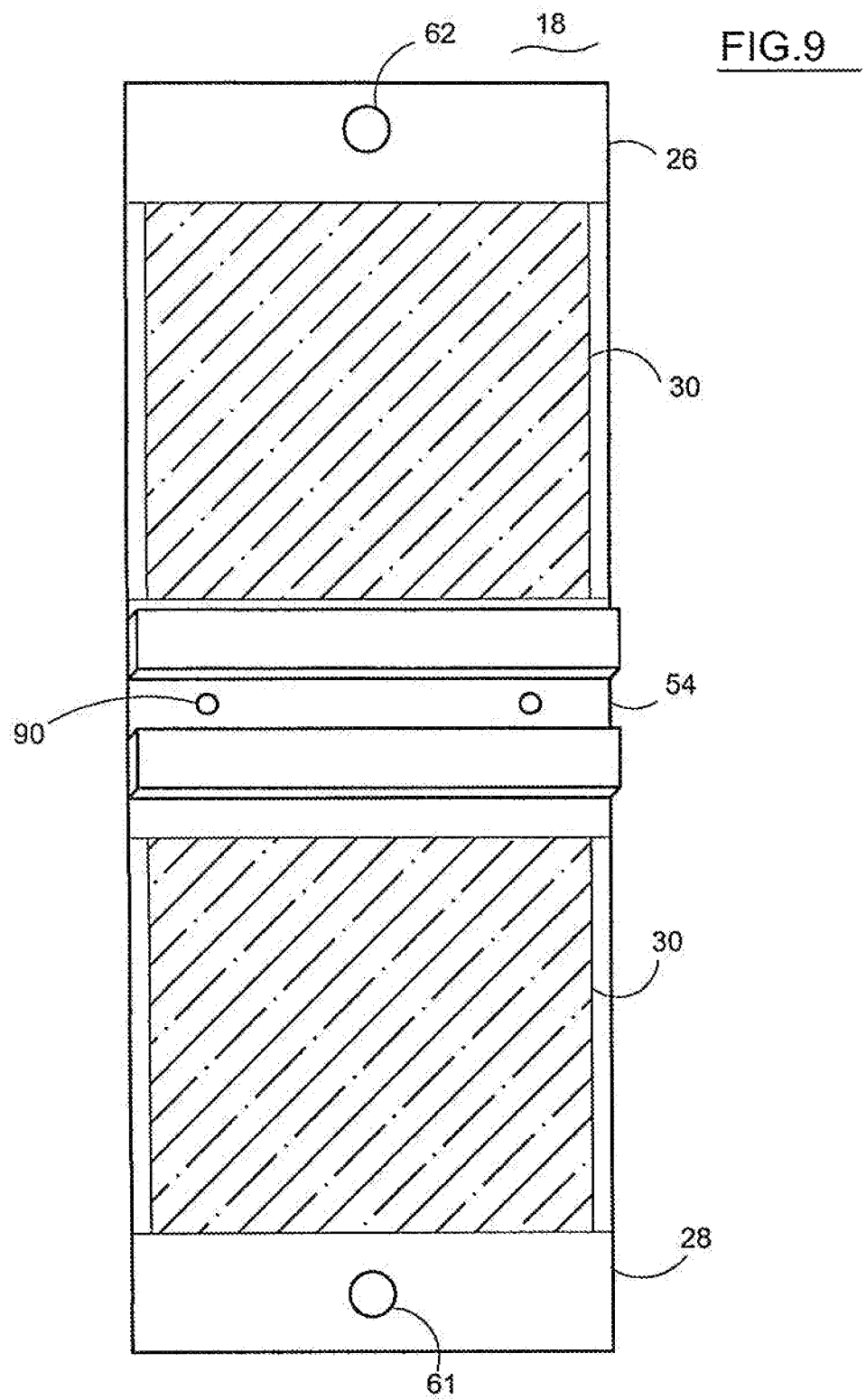
FIG. 9 is a plan view of the air quality test unit.

FIG. 9 is a plan view of the air quality test unit 18. The air quality test unit 18 is in a fully opened position, laying horizontal. Substrate panel 26 is shown connected to substrate panel 28 by hinge 54. Hinge 54 is connected to the substrate panels 26, 28 by any known attachment means. As shown in FIG. 5, the attachment means may be U-channel clamps or holders which receive and secure the substrate panels 26, 28 to the hinge 54. Within the hinge 54 are holes 90 for receiving one end of a clip 31 (not shown in FIG. 9). The holes 90 are placed on the portions of the hinge 54 closest to the outside edges. There are typically two holes 90, which receive a clip that is then attached to a ceiling vent. There are two other holes 61, 62, one in the distal end of each respective substrate panels 26, 28. The holes 61, 62 serve as alternate means for receiving one end of a clip 31 (not shown). When the air quality test unit 18 is to be used with a floor or wall vent, the clips 31 are secured within holes 61, 62 and then each clip is attached to a vent blade so that the air quality test unit 18 takes a v-shape form with the stick surfaces 30 on the inner side of the panels 26, 28 and directly in the path of the air flow.

Figure 10:
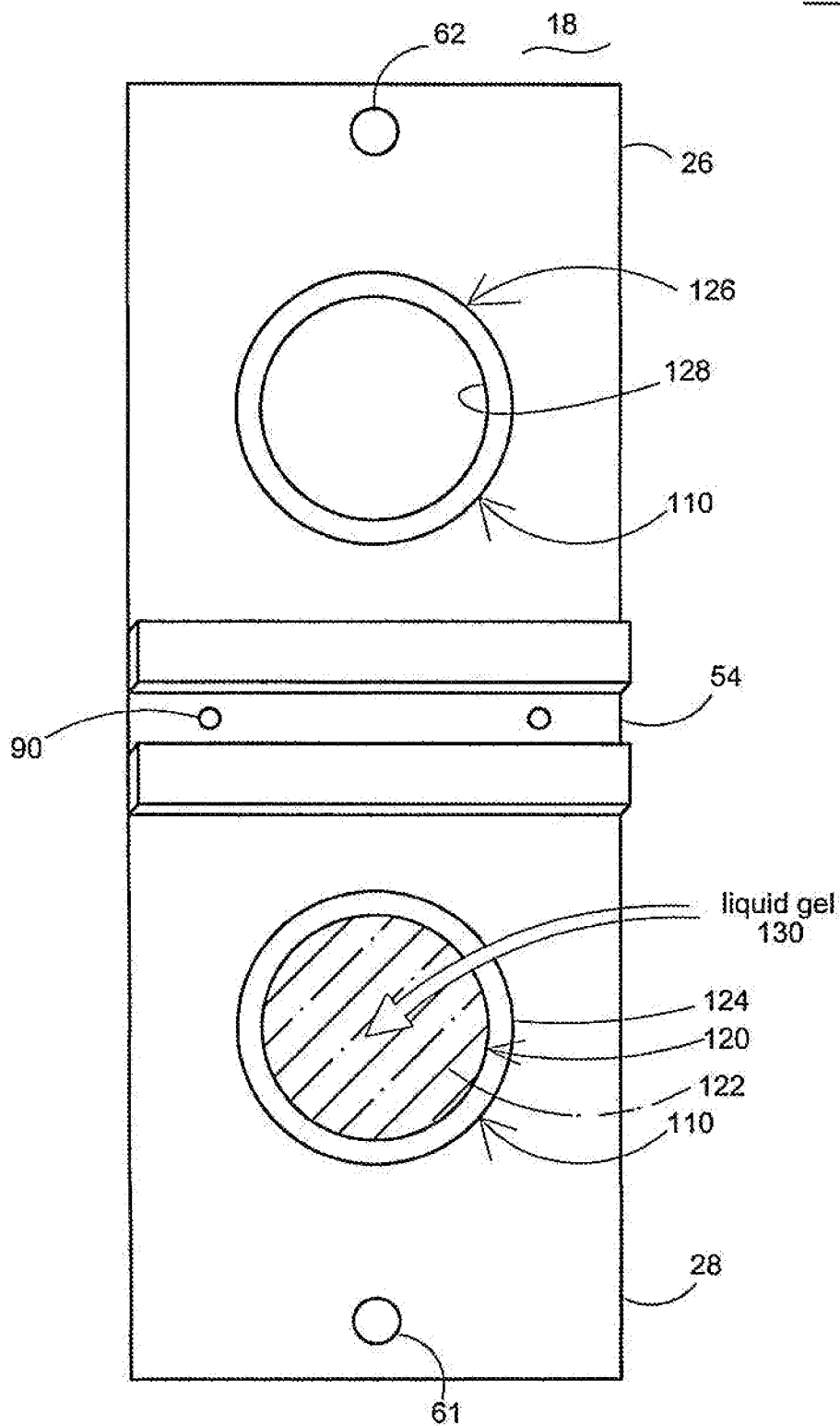
FIG. 10 is a plan view of an alternate embodiment of the air quality test unit with a two part collection container. (The rectangular substrate panels may be round and match the size and shape of the collection container outer planar walls, except for some tabs or extensions for the vent clip connectors. Other substrate panel shapes may be used.).

FIG. 10 is a plan view of an alternate embodiment of the air quality test unit 18. In this embodiment, a collection container 110 (best shown in FIG. 11), formed by collection base 120 and collection top or cover 126, is attached to the substrate panels 26, 28. As explained earlier, the planar base of the collection container may be part of substrate panel or consist of the entire substrate panel (the substrate panel shape is not an important feature of the invention, closure of the collection container is a relevant feature). In the illustrated embodiment, collection base 120 of the collection container 110 is attached to the substrate panel 28. The container base 120 includes an outer wall surface 124 that protrudes out from the collection pad panel 28 in a perpendicular fashion to form a "petri dish-like" structure. The interior surface of the planar bottom of the collection base 120 contains a culture-growth medium collection pad 122. The growth medium collection pad 122 may be a fabric, cloth, sterile material, or paper material or otherwise suitable material for acting as a growth and/or capture substrate for the gel/liquid growth culture. The growth collection pad 122 is adhered to the bottom of the collection container 110. In one embodiment, the growth substrate 122 is a thin fibrous material that contains dehydrated culture media and/or a cold water-soluble gelling agent in a non-woven cloth matrix 122. The growth pad 122 is rehydrated for use with a liquid 130, such as a phosphate buffer.

Further, the collection pad 122 can be replaced with a specially designed surface layer or element that is disposed on the bottom surface of the collection part base 120. In other embodiments, the surface of collection base 120 can be roughened or printed to capture and retain the growth gel added into the container base by the user, prior to capturing the airborne contaminants. The designed surface layer/element or the roughened—printed surface retains the growth gel/liquid on the collection base 120 during acquisition of the airborne contaminants. The culture growth medium can be 3-D printed onto the collection base 120. The liquid or gel 130 may be a buffer that when added to the collection base 120 rehydrates and activates a dehydrated culture growth medium that is disposed on the cloth-like matrix or the adhering surface or a 3-D printed surface.

A liquid or gel or liquid substance 130 is added to the collection container 110 just prior to use and exposure to the airborne contaminants. The liquid substance 130 may be a liquid culture growth medium, such as a liquid agar or the like, which keeps the collected bacteria, yeast or mold alive until the unit is tested. The liquid substance 130 may be any known culture growth medium, a liquid gel or a substance that acts as a growth medium or serves to appropriately provide sustenance for the captured bacteria, yeast or mold until the collection container is tested. Agar is generally known to mean a gelatinous colloidal extract of a red algae (as of the genera Gelidium, Gracilaria, and Eucheuma) used especially in culture media of bacteria and other cells for diagnostic or laboratory experimental purposes. When the growth collection pad 122 is a thin fibrous material that contains dehydrated culture media and/or a cold water-soluble gelling agent in a non-woven cloth matrix, then the liquid 130 serves to rehydrate the growth substance and could be a saline or a phosphate buffer or the like. The collection container 110 could alternatively contain a solid culture growth medium in the base 120 of the collection container 110. A cover 126 to the collection container 110 (see FIG. 11) is located on the substrate panel 26 in FIG. 10. The collection container cover 126 contains an inner wall 128 that protrudes out from the substrate panel 26 perpendicularly.

The air quality test unit 18 with the collection container 110 attaches to the vent in the same way as the prior described embodiment with the sticky surfaces 30 as shown in FIGS. 1A, 1B, and 2. The collection container 110 will be placed in the airflow 14. Similar to FIGS. 1A and 1B, when used on a wall vent or floor vent, the collection container 110 would be on the inside of the V-shaped configuration formed by the substrate panels 26, 28 being attached to the vent 16 by clips 31. Similar to FIG. 2, when used on a ceiling vent, the collection container 110 would be on the outside of the V-shaped configuration formed by the substrate panels 26, 28 being attached to the vent 16 by clip(s) 31 through the holes 90 in the hinge 54. As shown in FIG. 10, within the hinge 54 are holes 90 for receiving one end of a clip 31 (not shown in FIG. 10). The holes 90 are placed on the portions of the hinge 54 closest to the outside edges. There are typically two holes 90, which receive a clip that is then attached to a ceiling vent. There are two other holes 61, 62, one in the distal end of each respective substrate panel 26, 28. The holes 61, 62 serve as alternate means for receiving one end of a clip 31 (not shown). When the air quality test unit 18 is to be used with a floor or wall vent, the clips 31 are secured within holes 61, 62 and then each clip is attached to a vent blade so that the air quality test unit 18 takes a v-shape form with the collection container 110 on the inner side of the panels 26, 28 and directly in the path of the air flow.

After accumulation of the airborne contaminants, the collection container is closed by rotating the substrate panels together. As shown in FIG. 11, when the air quality test unit 18 is moved to a closed position, substrate panels 26 and 28 are rotated toward each other, and the inner wall 128 of the cover 126 fits around the outer wall surface 124 of the collection container base 120 to substantially sealingly close the collection container 110 and form a substantially airtight collection container 110. When the panels 26, 28 are closed, the inner wall 128 of cover 126 fits around the outer wall surface 124 of the collection container base 120 in an interference fit. The substantially airtight closed collection container 110 will allow the airborne substances to remain intact and alive until the air quality test unit 18 may be tested. The culture growth causes the contaminants to grow in some situations.

The alternative embodiment using a collection container 110 on the substrate panels 26, 28 to collect a sample involves the use of a liquid substance 130 that must be added to the growth collection pad 122 just prior to use of the air quality test unit 18. Once the liquid substance 130 is added, the air quality test unit may be hung on the vent. The air quality test unit 18 of the alternative embodiment is preferably hung from the vent for a short duration of time, so that the liquid substance 130 does not dry out. In a preferred embodiment, the air quality test unit 18 that includes a collection container 110, will be hung on the vent for 30 minutes, then removed and sent out for testing. Although a liquid culture growth medium is discussed in this embodiment, other culture growth systems may be used such a culture growth medium shielded from the ambient air prior to use by a removable covering (see FIG. 3).

Rather than use a culture growth medium in the collection container 110, the airborne contaminants may be captured on an adhesive surface and the collection container closed prior to shipment to the lab and further lab analysis.

Figure 12A:
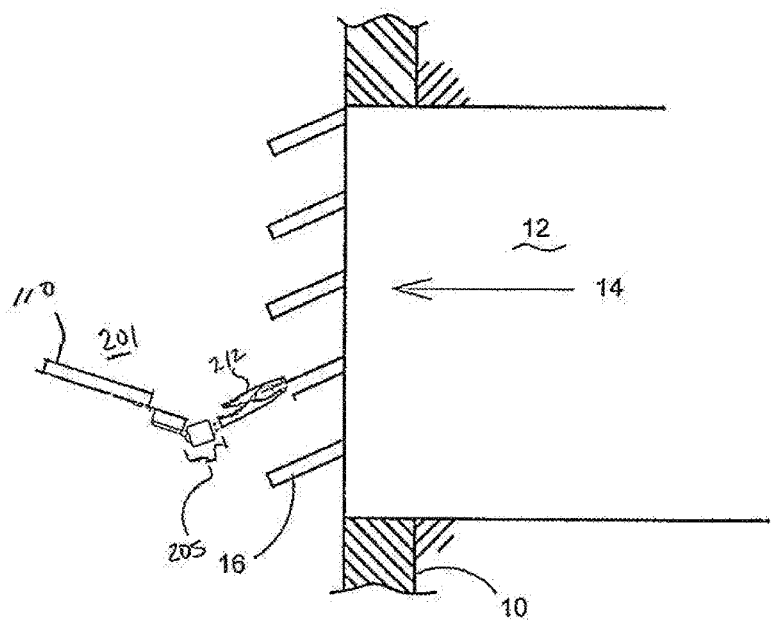

As shown in FIGS. 12 A and 12B, an alternate embodiment of the air quality test unit 201 uses one substrate panel with a collection container with a removable cover. While in a collection mode, the cover is removed to expose the collection pad. Prior to analysis by a lab, the cover is placed over the collection pad and is shipped to the laboratory for analysis of air borne particles and contaminants. FIG. 12A is a side view of a HVAC wall duct 12 and vent 16 with an air quality test unit 201 attached to the vent blades 16 or vent vanes. FIG. 12A shows the AQ kit with the cover removed. The vent blades 16 channel air from the HVAC duct work 12 into the interior space of the building. FIG. 12A shows the HVAC duct 12 carrying air flow 14 towards and out of the vent 16. In FIG. 12A, the vent is in the wall 10. In some building construction, typically in warmer, southern climates, the HVAC ducts are located in the ceilings and walls such that vents can be placed either in the ceilings or the walls of the building.

Figure 12B:
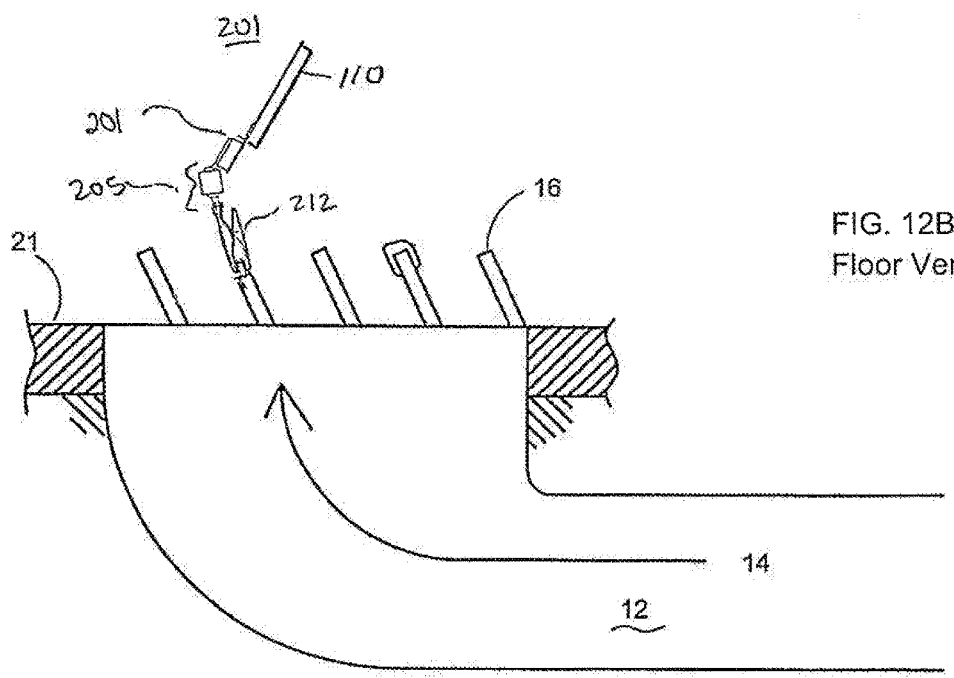

The air quality test unit 201 is removably attached to the blade of the vent 16. The air quality test unit 201 is made of one substrate panel, a collection container 110, universal pivot joint 205 or articulating joint and a clip 212. The air quality test unit 201 is designed with pivoting joints to allow the user to bend the collection container to the desired angle to the air flow 14. FIG. 12B shows a similar air quality test unit 201 attached to the vent blade wherein vent 16 is disposed in the floor 21. In building construction in colder, northern climates, HVAC duct work is placed under the flooring.

FIG. 13 is a front elevational view of an air quality test unit 201 with an axially aligned universal joint 205 and FIG. 14 is a perspective view of the air quality test unit 201 with the axially aligned universal joint 205. The planar base of the collection container may be part of substrate panel 28 or consist of the entire substrate panel (the substrate panel shape is not an important feature of the invention). In the illustrated embodiment, collection base 120 of the collection container 110 is attached to the substrate panel 28. The container base 120 includes an outer wall surface 124 that protrudes out from the collection pad panel 28 in a perpendicular fashion to form a "petri dish-like" structure. The interior surface of the planar bottom of the collection base 120 contains a collection pad 122. The collection pad 122 may be a fabric, cloth, sterile material, or paper material or otherwise suitable material for acting as a growth and/or capture substrate. The collection pad 122 could also be a cloth-like matrix, roughened or coarse-grained surface, adhering surface or a retaining matrix. In one embodiment, the collection pad 122 is a thin fibrous material that contains dehydrated culture media 122. The collection pad 122 is adhered to the bottom of the collection container 110. By way of example, the collection pad 122 could be those sold under the brand COMPACT DRY "YM"™ by Nissui Pharmaceutical, Co. Ltd. This collection pad is used to identify and quantify yeast and mold. It is composed of potato dextrose agar with a colored dye, specifically chromogenic enzyme substrate X-Phos.

The universal joint 205 allows the air quality test unit 201 to be bent such that the collection container 110 can be placed in the air flow 14. In one embodiment, as shown in FIGS. 12A and 12B the air quality test unit 201 is bent and angled into the air flow 14 through the ball and socket pivot joints 207, 208. The ball and socket pivot joints 207, 208 are placed on either side of a short connection tube 210. One ball and socket joint 207 is attached to the substrate panel 28 and the other ball and socket joint is attached to the clip 212. The substrate panel 28 with the collection container 110 is bent to an obtuse angle from the clip 212, such that the collection container 110 will be in the air flow when placed on the vent, as shown in FIGS. 12A and 12B. For example, the obtuse angle could be from 100 to 120 degrees. The angle will depend upon the particular angle of the vents. The pivot joints 205 or articulating joints will allow the user to align the collection container 110 in the ideal position, which is an acute angle or about a 45 degree angle to the air flow 14. This will allow air borne particles to adhere to the surface, without the substrate panel 28 blocking the air flow 14 or being in such direct air flow 14 that the air borne particles are blown off the collection pad 122. This will allow the collection container 110 to capture the maximum amount of air borne particles.

The use of an articulating vent-to-collection container arm permits the AQ test unit to be attached to floor vents, wall vents or ceiling vents such that the collection pad can be perpendicular to the air flow through the vent or at least at an acute angle to the air flow.

As shown in FIG. 15, the air quality test unit 201 has a detachable collection container cover 215 which fits over the collection container base 120. The air quality test unit 201 will be packaged with the detachable collection container cover 215 on the collection container 110. This will eliminate any chance of contamination before use. When the user is ready to test their air quality, they will remove the detachable collection container cover 120, bend the unit 201 to the desired angle, and attach the unit 201 to the vent blade. After gathering contaminants and airborne particles, the user closes the containment unit by re-mounting the cover over the collection pad.

The air quality test unit kit provides a user with an air quality test unit and a process for shipping the unit to the laboratory for testing. The kit ideally includes instructions for proper use and placement of the air quality test unit. The kit also may include packaging and labels for shipping to the laboratory that performs the testing. There may also be instructions or information for electronic payment for testing, arranging receipt of the air quality report electronically, and/or information on a laboratory website for arranging shipment and receipt of results.

While the preferred embodiment of the invention has been described using specific terms, such description is for illustrative purposes only, and it is to be understood that changes and variations may be made without departing from the spirit or scope of the following claims. The claims appended hereto are meant to cover modifications and changes within the scope and spirit of the present invention.

What is claimed is:

1. An air quality test unit for attachment to a vent of a heat, ventilation, air conditioning (HVAC) system with air flowing there through comprising:
    a substrate panel with a collection container;
    a collection pad disposed on a collection container base of the collection container;
    a detachable collection container cover;
    at least one pivot hinge coupling the substrate panel to a clip;
    the clip secured to the at least one pivot hinge and adapted to attach to the vent; and
    wherein the collection cover is configured to be removed and the substrate panel is configured to be positioned in the air flow with the clip attached to said vent such that the collection container captures airborne substances in air flow from the vent.

2. The air quality test unit of claim 1, wherein the clip is configured to be detached from the vent after a predetermined time and the collection container cover is configured to be placed over the collection container.

3. The air quality test unit of claim 1, wherein the collection pad is a cloth-like matrix, roughened or coarse-grained surface, adhering surface or a retaining matrix.

4. The air quality test unit of claim 1, wherein the collection pad contains culture-growth medium.

5. The air quality test unit of claim 1, wherein the at least one pivot hinge are two pivot hinges coupling the substrate panel to the clip.

6. The air quality test unit of claim 1, where the at least one pivot hinge is a ball and socket pivot hinge.

7. The air quality test unit of claim 1, wherein the at least one pivot hinge allows the substrate panel with the collection container to be positioned at about a 100 to 120 degree angle from the clip.

8. The air quality test unit of claim 1, wherein the at least one pivot hinge allows the substrate panel with the collection container to be positioned at an acute angle to the air flow.

9. An air quality test unit for attachment to a vent of a heat, ventilation, air conditioning (HVAC) system with air flowing there through comprising:
    a substrate panel with a collection container;
    a collection pad disposed on a collection container base of the collection container;
    a detachable collection container cover; and
    at least one articulating hinge coupling the substrate panel to a clip, wherein the clip is adapted to attach to the vent.

10. The air quality test unit of claim 9, wherein the clip is configured to be detached from the vent after a predetermined time and the collection container cover is configured to be placed over the collection container.

11. The air quality test unit of claim 9, wherein the collection pad is a cloth-like matrix, roughened or coarse-grained surface, adhering surface or a retaining matrix.

12. The air quality test unit of claim 9, wherein the collection pad contains culture-growth medium.

13. The air quality test unit of claim 9, wherein the at least one pivot hinge are two articulating hinges coupling the substrate panel to the clip.

14. The air quality test unit of claim 9, where the at least one articulating hinge is a ball and socket pivot hinge.

15. The air quality test unit of claim 9, wherein the at least one articulating hinge allows the substrate panel with the collection container to be positioned at about a 100 to 120 degree angle from the clip.

16. The air quality test unit of claim 9, wherein the at least one articulating hinge allows the substrate panel with the collection container to be positioned at an acute angle to the air flow.

* * * * *